United States Patent [19]

Krogh

[11] 4,058,365
[45] Nov. 15, 1977

[54] PROCESS FOR AUTOMATIC TITRATION

[75] Inventor: Søren-Christian Krogh, Ganlose, Denmark

[73] Assignee: Radiometer A/S, Copenhagen, Denmark

[21] Appl. No.: 678,625

[22] Filed: Apr. 20, 1976

[30] Foreign Application Priority Data

Apr. 24, 1975 Denmark .............................. 1802/75

[51] Int. Cl.$^2$ ........................................... G01N 31/16
[52] U.S. Cl. ................................................. 23/230 R
[58] Field of Search .................. 23/230 R, 253 R, 259

[56] References Cited

U.S. PATENT DOCUMENTS 2,770,531 11/1956 Hawes et al. ....................... 23/230 R
2,950,178 8/1960 Halfter et al. ...................... 23/253 R
3,730,685 5/1973 Prohaska ............................ 23/230 R Primary Examiner—Robert M. Reese
Attorney, Agent, or Firm—Hubbell, Cohen, Stiefel & Gross

[57] ABSTRACT

A process for automatic titration wherein the dosage of titrant is controlled by a digital computer, the titration being started with at least one dosage of a preselected size, each dosage of titrant thereafter and throughout the total course of the titration being precalculated and controlled on the basis of transducer signal change per added titrant volume unit at the preceding dosages in such a way that the titrant dosages are relatively smallest around the equivalence point.

12 Claims, 3 Drawing Figures

PROCESS FOR AUTOMATIC TITRATION

BACKGROUND OF THE INVENTION

The present invention relates to a process for automatic titration of chemical systems.

Using a suitable transducer which generates signals that are a function of the condition of the chemical system and the change of this condition on addition of titrant, the process of the invention permits the determination of equivalence point or points in any chemical system, provided that the transducer, the chemical system and the titrant are so adapted to each other that the transducer signal change on titrant dosage of a certain size depends uniquely on the distance to the equivalence point. This condition is fulfilled for all potentiometric titrations, such as those which use, as a transducer, an ion-sensitive electrode (for example a pH electrode or an electrode which is selectively sensitive to ion or ions other than the hydrogen ion) or a redox-sensitive electrode, as well as for titrations using a chemical indicator which undergoes a color change in which the resultant optical density change is measured by using a photocell as the transducer.

The process of the invention permits an especially fast and accurate automatic titration of the chemical systems in question without requiring any prior knowledge of the course of the titration curve or the position of the equivalence point or points.

SUMMARY OF THE INVENTION

In the process of this invention, a transducer is used in the automatic titration of chemical systems in which the change in transducer signal ($\Delta S$) on titrant dosage of a fixed size ($\Delta V$) depends uniquely of the distance to the equivalence point. In the process of the invention, the titrant dosage is controlled by an electronic digital computer which records the absolute value of the transducer signal (S) at the time in question and the total added amount of titrant (V) at the time in question, and also corresponding values of titrant dosage ($\Delta V$) and transducer signal change ($\Delta S$), and the titration is started with at least one dosage of preselected size and thereafter, through the total course of titration, each titrant dosage is precalculated and controlled on the basis of the transducer signal change per added titrant volume unit ($\Delta S$)/($\Delta V$) at preceding dosages in such a way that the titrant dosages are relatively smallest around the equivalence point.

Due to the precalculation of titrant dosage performed at all times throughout the total course of titration, it is possible to add large dosages of titrant at the points where the titration curve has a relatively flat course, in order that the system will approach the equivalence point fast and without superfluous intermediate stations, while on the other hand the titrant dosages in the proximity of the equivalence point are made so small that an exact determination of the equivalence point is obtained.

DETAILED DESCRIPTION OF THE INVENTION

In the process of the invention, the equivalence point is suitably determined in the following manner: subsequently to each dose of titrant, the computer calculates the second order difference quotient or second derivative $$\frac{\Delta \left( \frac{\Delta S}{\Delta V} \right)}{\Delta V}$$

and records and stores this value with its sign, and when a change of the sign of this second derivative after a titrant dosage has been ascertained occurs, which is an indication that the equivalence point has been passed, a digital computer interpolates to a more exact determination of the titrant amount corresponding to the equivalence point, such as is described in greater detail below. It is evident that the decisive parameter in this connection is the sign of the second derivative, and that it is not necessary to calculate the numerical value of the second derivative for this purpose; for example, instead of division with $\Delta V$, division with a fixed arbitrary constant of fixed sign could be thinkable. Although it would, using the principles of the present invention, be possible to perform additional titrant dosages subsequently to the ascertainment of the change of sign of the second derivative and before performing the interpolation, it has been found that this does not lead to any special additional advantages, and in titration procedures where the titration is considered finished when one equivalence point has been reached, such additional dosage or dosages would merely increase the time necessary for the titration operation.

Since the course of the titration curve in the process of the invention is determined on the basis of relatively few points, it is important that these points have a high degree of reliability, and hence, according to the invention, it is desirable that after each titrant dosage, a time interval is allowed to pass before the transducer signal is accepted. Preferably, the desired reliability of the transducer signal is obtained in such a manner that the computer compares the fluctuations of the transducer signal with a predetermined permitted variation and accepts the transducer signal when it has attained the desired stability, that is, lies within the allowed variation range. Another possibility is that the computer is adapted to allow for a certain period to pass after each titrant dosage, before the transducer signal is accepted, and finally, a combination of the variation and the time criteria may be used in that the transducer signal is accepted as soon as it is within the allowed variation breadth, but if it does not become within the allowed variation breadth, then it is simply accepted at the expiration of a predetermined maximum period.

The interpolation performed after a change of sign of the second derivative may use any interpolation principle suitable for ascertaining the exact total amount of titrant at the point of change of sign of the second derivative with sufficient exactitude and in consideration of the typical course of a titration curve. According to the invention, it has been found suitable to perform the interpolation for the determination of the equivalence point on the basis of the expression $$V_{eq.} = V_4 - \Delta V_{3,4} - \Delta V_{2,3} \frac{num \cdot \beta}{num \cdot \beta + num \cdot \alpha}$$

wherein $V_{eq.}$ is the total amount of titrant at the equivalence point, $V_4$ is the total added amount of titrant at the calculation time, $\Delta V_{3,4}$ is the titrant dosage immediately preceding the calculation time, in other words, the last titrant dosage performed, and $\Delta V_{2,3}$ is the titrant dosage immediately prior to $\Delta V_{3,4}$, in other words, the titrant dosage after which the change of sign of the second derivative was ascertained, whereas num.$\alpha$ is the numerical value of the second order difference quotient $$\frac{\frac{\Delta S_{2,3}}{\Delta V_{2,3}} - \frac{\Delta S_{1,2}}{\Delta V_{1,2}}}{\Delta V_{1,2} + \Delta V_{2,3}}$$

(wherein $\Delta S_{2,3}$ is the transducer signal change corresponding to $\Delta V_{2,3}$, $\Delta V_{1,2}$ is the titrant dosage immediately prior to $\Delta V_{2,3}$, and $\Delta S_{1,2}$ is the transducer signal change corresponding to $\Delta V_{1,2}$) and num.$\beta$ is the numerical value of the 2nd order difference quotient $$\frac{\frac{\Delta S_{3,4}}{\Delta V_{3,4}} - \frac{\Delta S_{2,3}}{\Delta V_{2,3}}}{\Delta V_{2,3} + \Delta V_{3,4}}$$

(wherein $\Delta S_{3,4}$ is the transducer signal change corresponding to $\Delta V_{3,4}$).

It will be noted that for the purpose of the present invention, it is necessary and sufficient that the computer stores, during the total course of titration, the last three corresponding values of $\Delta S$ and $\Delta V$ and the last absolute value of the transducer signal and the total amount of dosed titrant connected thereto.

The decisive feature to the efficiency and speed of the process according to the invention is the precalculation of each titrant dosage in such a way that the titrant dosages are relatively smallest around the equivalence point, and hence, the program according to which the computer precalculates the titrant dosages must be a program which ensures that the amount dosed is reduced when the titration curve becomes steeper, and the more the curve bends towards an equivalence point. According to the invention, the following expression has been found suitable for this purpose:

$$\text{dosage}_{(n+1)} = \frac{a}{\left(\frac{\Delta S}{\Delta V}\right)_n + b + x} + c$$

wherein $$x = \left|\left(\frac{\Delta S}{\Delta V}\right)\right|_n - \left|\left(\frac{\Delta S}{\Delta V}\right)\right|_{n-1}$$

and is included in the above fraction only when the value thus calculated for $x$ is positive, whereas $a$, $b$, and $c$ are constants. It will be noted that $x$ results in the dosed amount being dependent upon the curve inclination at a point and the preceding point so that the amount dosed is reduced when the curve becomes steeper, and the more the curve bends towards an equivalence point, while the constants $b$ and $c$ ensure both an upper and a lower limit for the amount dosed. In practice it has been found that suitable values for $a$, $b$, and $c$, respectively, are 300, 0.4, and 10, respectively, when using an automatic burette equipment which at total emptying of the burette produces 5000 counts, and the transducer signal optimally comprises 10,000 counts through the course of titration.

In the process of the invention, the computer may be adapted to stop the titration when an equivalence point has been ascertained and calculated, or to proceed with the titration for the ascertainment of possible additional equivalence points; in the latter case, the titration may be continued until the burette is empty, or until the desired amount of equivalence points has been ascertained and calculated. Here again, the process of the invention will show its characteristic advantages, as the process from one equivalence point towards the next equivalence point will take place in individually precalculated dosage amounts which are large as long as the transducer signal change per titrant dosage is small.

Due to the individual pre-calculation, in each and every increment, of the titrant dosage, which is large as long as the titration curve has a relatively flat course, but becomes increasingly smaller when the curve bends and becomes steeper (and, if titration is continued after an equivalence point, becomes larger again on the flat curve section following), a fast titration with retention of the necessary exactitude is obtained. As a microburette of the kind which will be used in most practical embodiments of the process of the invention may be emptied very rapidly, the largest contribution to the time consumption in the titration of the process of the invention will be the time which passes before the transducer signal is accepted subsequently to each titrant dosage, and hence, it is essential that the number of dosages and, accordingly, of periods in which stability is to be waited for, may be kept very low in the process according to the present invention, without any consequent loss of exactitude.

German Offenlegungsschrift No. 2,320,193 and the corresponding U.S. Pat. No. 3,730,685 disclose a process for automatic determination of the equivalence point in a potentiometric titration of a solution by means of an electronic digital computer, and the said process comprises various features which resemble the process of the present invention, including, for example, waiting for stability subsequently to each titrant dosage, determination of the proximity of the equivalence point on the basis of a calculation of the difference quotient and reduction of the amount of titrant when the equivalence point is near, and also calculation of the actual equivalence point by means of a mathematical equation.

However, in the process according to the said German Offenlegungsschrift and the said U.S. patent, the size of the single titrant dosages is kept constant within certain intervals, the size of each single dosage increment in each interval being pre-determined with regard to the system to be titrated, and the transition from an interval with a certain increment size to a next interval with a smaller increment size being performed when the difference quotient $\Delta S/\Delta V$ exceeds a certain value which is predetermined with regard to the specific system titrated. At a certain value of the difference quotient, the individual dosage increments are reduced to a minimum size which is thereafter kept constant during titration past the equivalence point and for a predetermined number (as a concrete example, 5 is mentioned) of additions subsequently to passing the equivalence point. While this procedure according to the German Offenlegungsschrift and the U.S. patent may be very suitable for systems in which the course of the titration curve is known in advance, the process of the present invention, as compared to the thus known process, shows the advantage that, due to the individual pre-calculation of each titrant dosage on the basis of the transducer signal change at preceding dosages, it will also function efficiently in cases where the course of the titration curve is unknown. Thus, for example, the titration curve may have a relatively flat course even at the equivalence point, and if this has not been considered in advance in the process according to the German Offenlegungsschrift and the U.S. patent, the titration with large increments may pass the equivalence point, and the equivalence point will then either not be detected at all, or it will be determined with less exactitude, while on the other hand at a different course of the titration curve it is possible that a change minimal dosages will occur too soon such that a very large numbers of increments in the interval employing such minimum dosages will be necessary before the equivalence point is reached. Furthermore, the minimum dosage selected may prove to be too large for an actual case. Finally, due to the method of calculation of the actual equivalence point, the technique described in the Offenlegungsschrift and the U.S. patent will require the establishment of a larger amount of points on the titration curve than in the process of the present invention, which causes added time consumption and added requirements to the storage capacity of the computer, and the Offenlegungsschrift and the U.S. patent give no indication as to how one would be able to determine possible additional equivalence points on the titration curve. Hence, the process of the present invention differs essentially and advantageously from the disclosure of the above-mentioned German Offenlegungsschrift and U.S. patent.

In the process of the present invention in which the equivalence point or points is/are determined by means of a small number of titrant dosages, the size of which is pre-calculated using the difference quotient $\Delta S/\Delta V$, and in which the position of the equivalence point is calculated using the second derivative or difference quotient of second order, it is, of course, important that the individual determinations of $\Delta S$ and $\Delta V$ are sufficiently reliable, and as a certain measuring inaccuracy will always be involved, it is fact—contrary to the teaching of the German Offenlegungsschrift and the above-mentioned U.S. patent — desirable that the individual dosages do not become too small, as the calculations may become uncertain if $\Delta V$ and, consequently $\Delta S$, become very small. A suitable size of the individual dosages is secured by suitable selection of the above-mentioned constants $b$ and $c$. Furthermore, it is preferred according to the present invention that the computer judges the quality or usefulness of the individual measured points, which may, for example, be obtained in the manner that a measured point which gives rise to a change in $\Delta S/\Delta V$ of less than a predetermined minimum value, for example 10%, in relation to the preceding $\Delta S/\Delta V$, is left out of consideration, there being then given an extra dosage, for example of 25% of the last $\Delta V$, whereafter the new measured point is accepted if the total value of $\Delta S/\Delta V$ from the last accepted measured point and to and including the new measured point exceeds the minimum value.

Apart from the advantages of an especially fast titration, even in systems in which the course of the titration curve is unknown, the process of the invention offers the advantage that it is not necessary to perform any calibration of the transducer used, as the process always works on the basis of transducer signal differences. This means that the manipulation of the system via the computer becomes extremely simple and in most practical cases involves only pressing a start button. However, if desired, the computer may be designed such that it may optionally be set to calculate a single equivalence point and thereafter stop the titration, or to calculate a first equivalence point and thereafter proceed with the titration, searching after a second or more equivalence points and terminate the titration after calculation of a selected number of equivalence points, or proceed with the titration until the burette is empty, or to stop the titration when a pre-selected end point value of the transducer signal has been passed. The last-mentioned end point criterion may also be elaborated so as to include an interpolation to determine the exact titrant consumption at the end point, in accordance with the expression:

$$V_{end} = V_4 - \frac{S_4 - S_{end}}{\Delta S_{3,4}} (\Delta V_{3,4})$$

wherein $V_{end}$ is the calculated amount of consumed titrant at the end point, $V_4$ is the total added amount of titrant at the calculation time, $S_4$ is the transducer signal value at the calculation time, $S_{end}$ is the pre-selected end point transducer signal value, $\Delta V_{3,4}$ is the titrant dosage immediately preceding the calculation time, in other words, the last titrant dosage performed, and $\Delta S_{3,4}$ is the transducer signal change corresponding to $\Delta V_{3,4}$. In some cases, the end point criterion may also be the main criterion, in other words, the process may also be performed in such a way that the computer does not detect equivalence points but merely titrates to an end point, calculated, e.g. as described above, or the system may be adjusted so as to both titrate to an end point and calculate any equivalence points passed, and in all cases, the above-mentioned advantages of the process of the invention will be obtained. In connection with end point titration it is in some routines customary to perform several titrations in one titration vessel, merely introducing the new sample in the titrated sample remaining from the prior titration. When using the process of the present invention for such end point titration, the surplus titrant added in excess of the end point volume might give rise to disadvantages in such routine, but this disadvantage can of course simply be obviated by having the computer automatically correct for the overtitration, that is, prior to the determination of a new point titrant volume value, the computer automatically adds the surplus of the prior titration to the said point volume value.

As mentioned above, it has been found that the process of the invention gives an extraordinarily fast course of titration and very reliable results, and it has also been found that, using the process of the invention, it is possible, with great exactitude, to titrate even notoriously difficultly titratable systems in which the changes around the equivalence point are so relatively weak that they can hardly be determined on a plotted titration curve. This permits fast and exact automatic titration of chemical systems which can only with difficulty be titrated manually, for example titration of citric acid with sodium hydroxide.

DETAILED DESCRIPTION OF THE DRAWING

Figure 1:
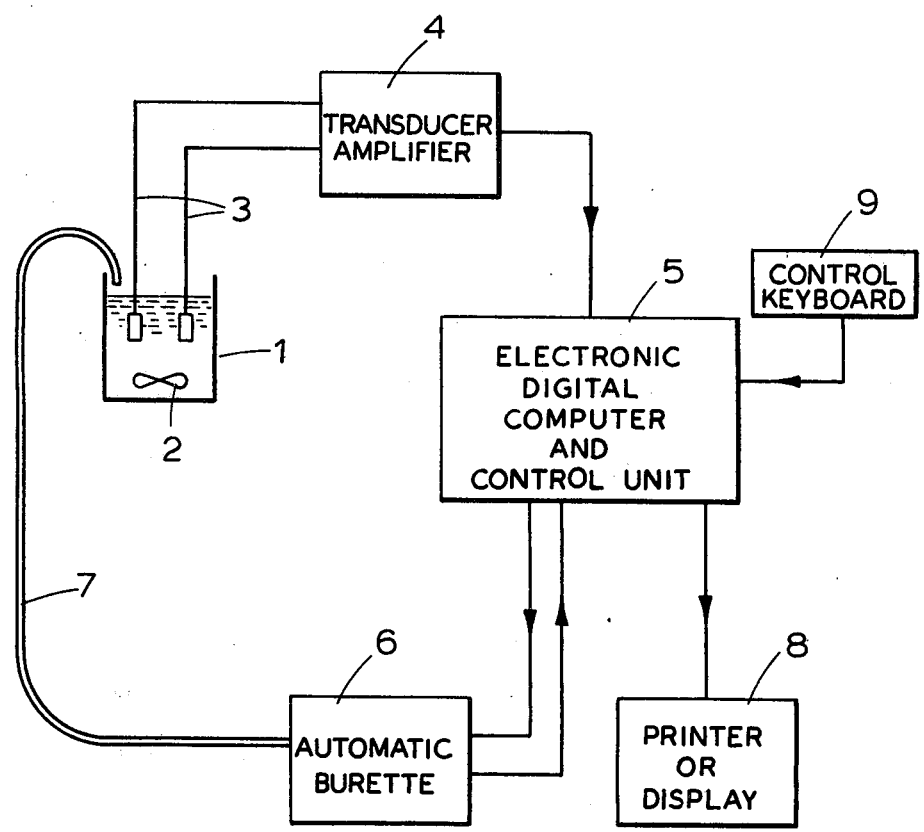
FIG. 1 shows, schematically, an apparatus for performing the process of the invention.

Reference is made to FIG. 1.

The liquid to be titrated is present in a titration vessels which may, if desired, be supplied with a stirrer 2, for example a magnetic stirrer. The transducer producing signals, the size and size changes of which are a function of the changes in the chemical system taking place during the titration, is exemplified as a set 3 consisting of an ion-sensitive electrode with matching reference electrode. As mentioned above, also a wide selection of other transducers may be used in the process of the present invention; for example, the transducer may be a photocell which in a manner known per se records color changes in the system to be titrated, to which there may have been added a chemical compound undergoing color changes during the titration course and serving as an indicator. The signal from the transducer 3 is led to a transducer amplifier 4, and the amplified signal in digital form is led to an electronic computer and control unit 5. A suitable automatic burette 6, which may be of a known design, and which may be connected in a manner known per se to the electronic computer and control unit 5, may, for example, comprise a motor-driven piston burette from which titrant is passed through a tube 7 to the titration vessel 1 when the motor is running. When the electronic computer and control unit causes the motor in the automatic burette 6 to run, titrant is dosed into the titration vessel 1, and concomitantly, the electronic computer and control unit records the amount of titrant currently dosed. When the desired amount of titrant has been dosed, the computer and control unit 5 cause the motor of the automatic burette to stop and record any surplus dosed before the motor actually stops. Hence, the electronic computer and control unit 5 record corresponding sets of change in transducer signal and dosed titrant, and as mentioned above, at least three consecutive sets of corresponding values of change in transducer signal and titrant consumption corresponding thereto, and the last absolute value of the transducer signal, and the corresponding total amount of dosed titrant are stored in the computer and control unit. From the electronic computer and control unit 5, the results from the titration are sent to a printer or display 8. The printer may, for example, be designed such that it prints corresponding values of titrant amount and transducer signal together with information as to the titrant amounts at the equivalence points found. A digital display may be designed such that it currently states added titrant amount or the size of the transducer signal, whereafter, when an equivalence point has been ascertained, it states the titrant consumption at the equivalence point. Evidently, the parameters here stated are only examples; of course, the computer and control unit may also be adapted so as to state, on the basis of the measured values and introduced information about the chemical system being titrated, other parameters calculated on the basis of the values found and the equivalence point calculated, for example the concentration of a certain component in the liquid being titrated. A control keyboard 9 may in a simple embodiment merely comprise a start button, but may in other embodiments comprise keys for entering additional information and/or orders, for example information about the chemical system titrated and orders concerning desired conversions based on the values found and the equivalence points calculated, orders concerning the duration of the titration, that is, whether only the first equivalence point is to be found, or whether additional equivalence points are to be sought for, or whether the titration should possibly be continued until the burette is empty, etc. Due to its speed and simplicity, the process of the invention is very well suited for use in connection with titration of large numbers of samples which are conveyed in special vessels in suitable automatic sample conveying apparatuses of known type.

A typical titration using the process of the invention proceeds as follows:

The start button 9 is pressed. The electronic computer and control unit 5 starts with setting the value zero in storage for total amount of titrant and determining whether the transducer signal is stable. If the change of transducer signal per time unit is not less than a certain value, the unit 5 waits until this stability has been obtained, or until a certain period of time has passed.

Thereafter, the computer and control unit 5 doses, by means of the automatic burette 6, a predetermined amount of titrant, for example 2% of the total burette content. When the transducer signal is acceptable, that is either when the change per time unit has become smaller than a predetermined value, or when a predetermined time period has passed, the change in transducer $\Delta S$ and the corresponding titrant consumption $\Delta V$, as well as the absolute value of the transducer signal S and the total titrant consumption V, are recorded and stored. The same amount of titrant is dosed, and stability is waited for as above, whereafter the change in transducer signal with corresponded titrant consumption are stored. The previously stored absolute value for transducer signal and the total amount of titrant are exchanged with the new values.

Thereafter, the computer 5 calculates the difference quotients of first order and of second order. The difference quotients of first order are suitably calculated numerically in order that up and down titration may be treated in the same manner. Thereafter, the computer 5 investigates whether the sign of the difference quotient of second order has changed and has become negative. By reasonable choice of titrant concentration in relation to the system to be titrated, this will of course not occur immediately after the second dosage. Thereafter, from the last recorded change of transducer signal and corresponding titrant consumption, a precalculation is made of the amount of titrant which is optimally dosed based on the desire of the fastest possible titration and the maximum titration exactitude. This precalculation can be made as described above. Thereafter, the computer 5 causes the automatic burette 6 to dose, whereby the precalculated amount of titrant plus any surplus is transferred to the titration vessel 1. The actually dosed titrant amount and the transducer signal change are recorded as described above, stability of the transducer signal being waited for. Thereafter, the difference quotients of first and second orders are calculated as described above, and investigation is made for any change of sign of the difference quotient of second order; if no change of sign has taken place, the titration proceeds, the next titrant dosage being precalculated as described.

When it is ascertained that the sign of the difference quotient of the second order has changed and has become negative, an equivalence point has been passed, and the exact position of the equivalence point is thereafter calculated by interpolation between values around the equivalence point, such as described above. During the total course of the titration, the reliability of the measured points is judged as described above.

When the equivalence point has been calculated, it is printed out and/or shown on the display 8.

Figure 2:
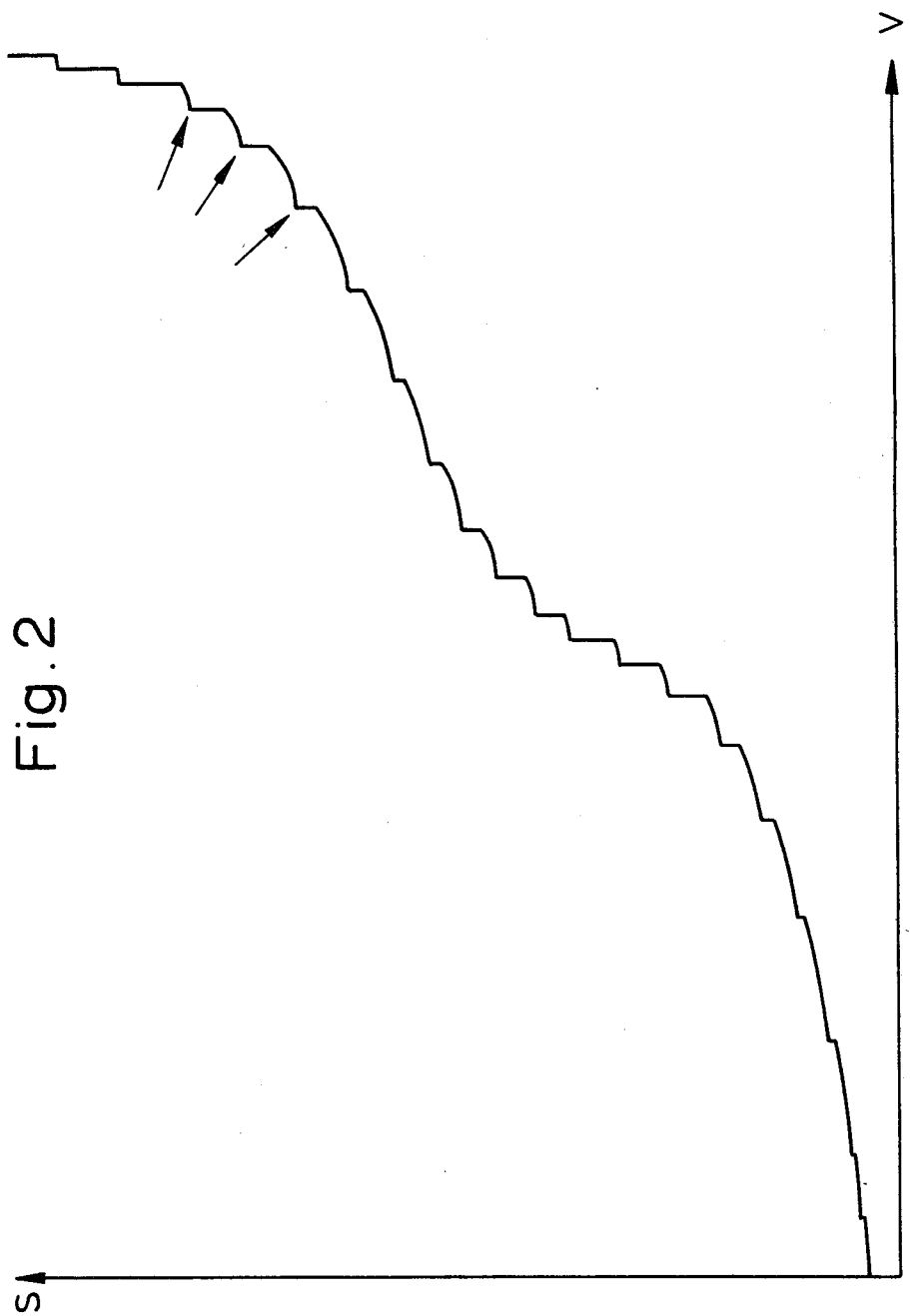
FIG. 2 and FIG. 3 are graphs showing the course of typical titrations performed using the present process.

A typical titration curve obtained using the process of the invention (corresponding values of S and V being plotted by means of a recorder coupled to the transducer amplifier 4 and the automatic burette 6) is shown in FIG. 2. The exact values for the titration appear from the below example 1. On the curve, the two starting dosages of same size are noted, and it is shown how the distance between two points on the curve (the actual curve points are at the top of the curve, compare, e.g., the points indicated by arrows) becomes smaller when the curve becomes steeper, and is smallest around the equivalence points. Noted is also the generally great distance between the points, permitting a fast titration with great exactitude in the determination of the equivalence point, as the change in transducer signal with corresponding titrant consumption will be determined relatively more exactly, the greater is the change in transducer signal and titrant consumption, respectively (within reasonable limits), whereby also the second derivative and, consequently, the equivalence point are determined more exactly.

Figure 3:
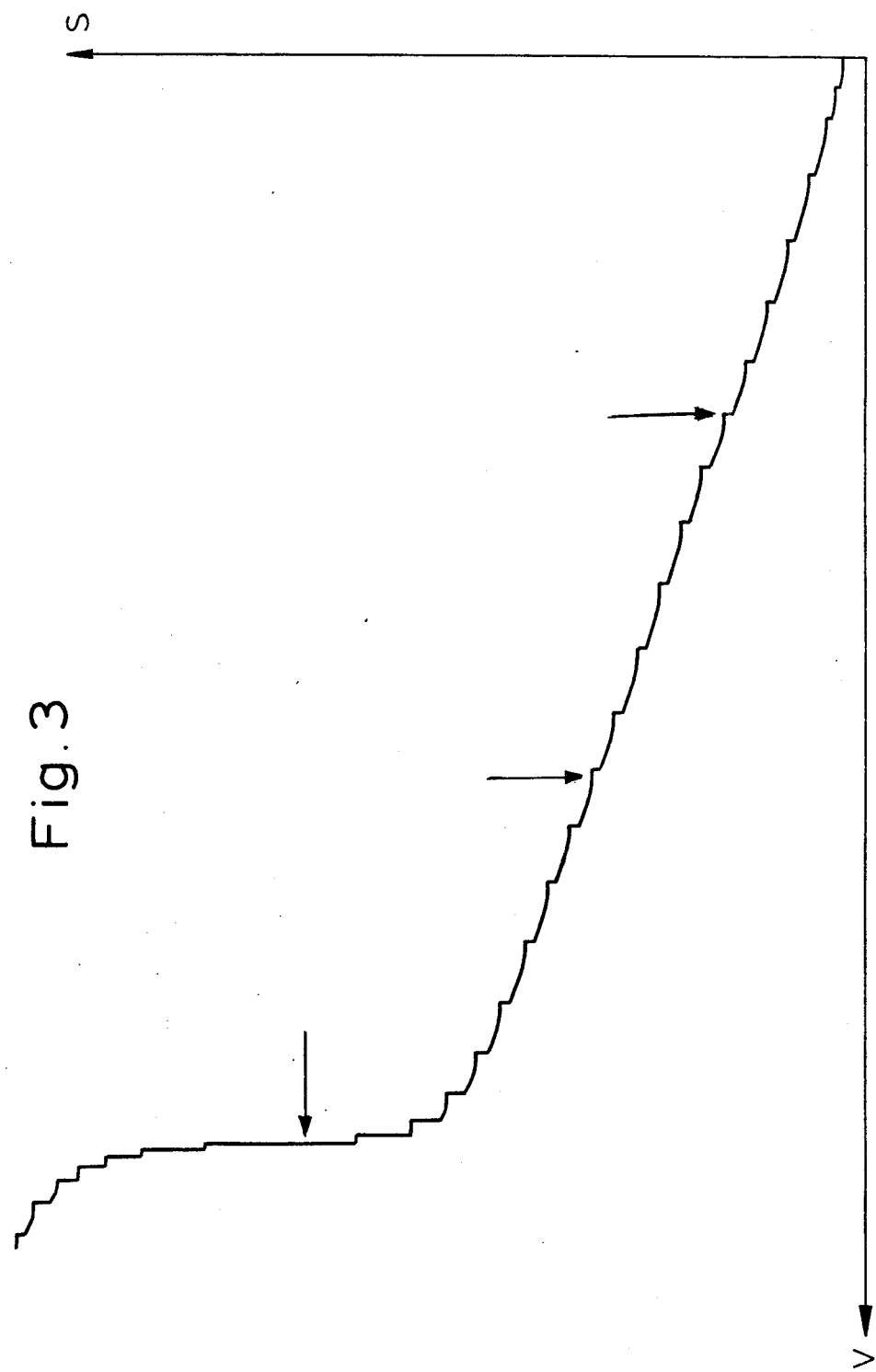

FIG. 3 shows a titration curve, plotted in the same manner as FIG. 2, the titration like the one in Example 2 (citric acid titrated with sodium hydroxide). It is to be noted that the curve comprises three equivalence points indicated by arrows. One of them is easily visible, but the two others are hardly visible and have yet been determined with great exactitude even with the relatively large increments apparent from the drawing.

EXAMPLES

Example 1

The apparatus used is as shown in FIG. 1. The liquid in the titration vessel is a mixture of 10 ml of a solution of $CaCl_2$ $MgCl_2$ which is about $10^{-3}M$ with respect to both calcium and magnesium and 4 ml of a buffer solution, pH 9.7 which is 0.05M with respect to dihydroxybenzoic acid and 0.05M with respect to glycine. The titration vessel with stirrer pertains to a titration assembly TTA 3 (Radiometer A/S, Copenhagen). The transducer system used is a reference electrode K 401 (Radiometer A/S, Copenhagen), and a calcium-sensitive indicator electrode F 2112 Ca (Radiometer A/S, Copenhagen), and the transducer amplifier used is a digital pH meter PHM 64 (Radiometer A/S, Copenhagen). The titrant used is a 0.1M solution of the sodium salt of ethylene diamine tetraacetic acid (EDTA $Na_2$) in a 250 /$\mu$l burette pertaining to an automatic burette with digital output (ABU 13, Radiometer A/S, Copenhagen). The computer and control unit and the printer are a PRS 10 (printer with built-in computer, Radiometer A/S, Copenhagen) which is programmed for the purpose.

The exact course of the titration curve, plotted as described above, appears from FIG. 2.

Equivalence points are calculated at 103.52 and 198.93 $\mu$liters of titrant, respectively, corresponding to transducer signal values at the equivalence points of 4.584 and 7.123, respectively, expressed as pCa. It is, by the way, remarkable that it is possible to determine absolute amounts of Ca and Mg in a solution of the kind in question, as they are notoriously difficult to separate. It has been found that due to the great resolving power of the process according to the invention, it is possible to determine the absolute values of Ca and Mg in systems of the kind described above containing Ca and Mg in relative amounts between 1:20 and 20:1.

It appears from FIG. 2 that in the present case, the computer and control unit has been adjusted to terminate the titration immediately after the calculation of the 2nd equivalence point.

Titrations of this and similar kind have been performed in a number of several thousands using the process of the present invention, and the reproducibility of the process of the invention has been found to be so good that the standard deviation is only $\pm 0.2\%$.

Example 2

The apparatus used is the same as in example 1 except that the indicator electrode is a pH-sensitive electrode (glass electrode) G 202 C (Radiometer A/S, Copenhagen), and the burette is a 2.5 ml burette. The liquid in the titration vessel is a mixture of 10 ml 0.03M citric acid and 10 ml water, and the titrant is a 0.5M aqueous NaOH solution. Under identical conditions, 20 titrations are performed, and it is found that with a total consumption of 1600 $\mu$liters of titrant, the standard deviation is as follows:

first equivalence point: 1.8 $\mu$liter
second equivalence point: 4.3 $\mu$liter
third equivalence point: 0.8 $\mu$liter In other words, a uniquely exact determination is obtained in all cases. It will be seen that the largest value of the standard deviation is still less than 1% compared to the amount of titrant used between the equivalence points.

The exact course of a titration curve corresponding closely to this example, but with the use of a total consumption of about 1900 $\mu$liters of titrant, is shown in FIG. 3.

It is to be noted that in this notoriously difficult titration with two very weak equivalence points, the total titration is terminated after about 3 minutes, and like in example 1, the only operation of the titration system was to press the start button; not one single parameter has to be individually adjusted.

What is claimed is:

1. A process for controllably obtaining titration in a chemical system by automatic control of successively provided titrant dosages to said chemical system after provision of at least one initial preselected size of titrant dosage, said process comprising the steps of successively sensing a total of said titrant provided as a result of each of said successively provided dosages up to the time of the most recent provided dosage and successively providing a titrant dosage signal change $\Delta V$ to a process controller each time in response to the most recent provided dosage at said time, successively detecting a change in chemical condition of said chemical system in response to each of said provided dosages and providing a transducer signal change $\Delta S$ to said process controller in response to each said detected change in condition, and successively controllably varying the size of each of said successively provided dosages by said process controller each time in response to at least the most recent of said provided transducer signal changes $\Delta S$ and said provided titrant dosage signal change $\Delta V$ which corresponds to said provided transducer signal change $\Delta S$ at said time for successively reducing each of said titrant dosage sizes as the relationship $\Delta S/\Delta V$ increases and for increasing each of said titrant dosage sizes as said relationship $\Delta S/\Delta V$ decreases, whereby the titrant dosage size each time is a function of at least the most recent relationship $\Delta S/\Delta V$ at said time.

2. A process in accordance with claim 1 wherein said process controller is a digital computer.

3. A process in accordance with claim 1 further comprising the steps of successively sensing said increases and decreases in said relation $\Delta S/\Delta V$ and continuing said titration by successively controllably varying the size of each of said successively provided dosages by said process controller until a decrease in said relationship $\Delta S/\Delta V$ has been sensed after an increase in said relation $\Delta S/\Delta V$ has been sensed, whereby an equivalence point for said titration is provided.

4. A process in accordance with claim 3 wherein said chemical system is one in which said change in transducer signal $\Delta S$ corresponding to said titrant dosage change $\Delta V$ depends on the distance to said equivalence point at said time.

5. The process of claim 4 wherein the titrant dosage is controllably varied by said process controller in accordance with the expression $$\text{dosage}_{(n+1)} = \frac{a}{\left(\frac{\Delta S}{\Delta V}\right)_n + b + x} + c$$

wherein $$x = \left|\left(\frac{\Delta S}{\Delta V}\right)\right|_n - \left|\left(\frac{\Delta S}{\Delta V}\right)\right|_{n-1}$$

and is only included when it is positive, and $a$, $b$ and $c$ are empirical constants for a predetermined total number of counts for emptying of a burette used for said titration and a predetermined total number of counts for said transducer signal through the course of said titration, where $a$ is a value which insures large dosages when the corresponding titration curve is flat, $b$ is a value which insures a maximum titrant dosage and $c$ is a value which insures a minimum titrant dosage.

6. The process of claim 4, in which, during the total course of titration, at least the last three corresponding values of $\Delta S$ and $\Delta V$ and the last absolute value of the transducer signal and the corresponding total amount of titrant dosed are stored in the process controller during the total course of titration.

7. A process in accordance with claim 6 further comprising the step of retrievably storing at least the values of the three most recently successively provided transducer signal changes $\Delta S_{2,3}$, $\Delta S_{3,4}$ and the values of the three most recently successively provided titrant dosage signal changes $\Delta V_{1,2}$, $\Delta V_{2,3}$, $\Delta V_{3,4}$ in response to which said process controller controllably successively varies said successively provided dosage sizes, said process controller detecting the location of said equivalence point in response to said stored values in accordance with the expression $$V_{eq.} = V_4 - \Delta V_{3,4} - \Delta V_{2,3} \frac{\text{num} \cdot \beta}{\text{num} \cdot \beta + \text{num} \cdot \alpha}$$

wherein $V_{eq.}$ is the total amount of titrant at said equivalence point, $V_4$ is the total added amount of titrant at the time of said detection, $\Delta V_{3,4}$ is the titrant dosage immediately preceding said detection time, and $\Delta V_{2,3}$ is the titrant dosage immediately prior to $\Delta V_{3,4}$, num. is the numerical value of the expression $$\frac{\frac{\Delta S_{2,3}}{\Delta V_{2,3}} - \frac{\Delta S_{1,2}}{\Delta V_{1,2}}}{\Delta V_{1,2} \Delta V_{2,3}}$$

wherein $\Delta S_{2,3}$ is said transducer signal change associated with said titrant dosage $\Delta V_{2,3}$, $\Delta V_{1,2}$ is the titrant dosage immediately prior to $\Delta V_{2,3}$, and $\Delta S_{1,2}$ is the transducer signal change associated with said titrant dosage $\Delta V_{1,2}$, and num.$\beta$ is the numerical value of the expression $$\frac{\frac{\Delta S_{3,4}}{\Delta V_{3,4}} - \frac{\Delta S_{2,3}}{\Delta V_{2,3}}}{\Delta V_{2,3} + \Delta V_{3,4}}$$

wherein $\Delta S_{3,4}$ is said transducer signal change associated with said titrant dosage $\Delta V_{3,4}$.

8. The process of claim 4 wherein a difference quotient of second order $$\frac{\Delta\left(\frac{\Delta S}{\Delta V}\right)}{\Delta V}$$

is calculated by said process controller subsequently to each titrant dosage, and the equivalence point is provided by interpolation when this difference quotient of second order has changed sign.

9. The process of claim 8 wherein the equivalence point is provided after the titrant dosage which is immediately subsequent to the change of sign of the difference quotient.

10. The process of claim 4 wherein, after each titrant dosage, a period of time is allowed to pass before the transducer signal is accepted by said process controller.

11. The process of claim 10 wherein a desired stability of the transducer signal is waited for before the signal is accepted by said process controller.

12. The process of claim 11 wherein the period of time which is allowed to pass before the transducer signal is accepted has a predetermined maximum duration.

* * * * *

UNITED STATES PATENT OFFICE
CERTIFICATE OF CORRECTION

Patent No. 4,058,365  Dated November 15, 1977

Inventor(s) Søren-Christian Krogh

It is certified that error appears in the above-identified patent and that said Letters Patent are hereby corrected as shown below:

Column 1, line 36: "uniquely of the" should read -- uniquely on the --.

Column 5, line 9: "change minimal" should read -- change to minimal --; line 10: "numbers" should read -- number --; line 38: "it is fact" should read -- it is in fact --.

Column 6, lines 44-45: "new point" should read -- new end point --.

Column 7, line 1: "vessels" should read -- vessel 1 --.

Column 8, lines 22-23: "transducer $\Delta$s" should read -- transducer signal $\Delta$s --; line 28: "corresponded" should read -- corresponding --.

Signed and Sealed this

Twenty-seventh Day of June 1978

[SEAL]

Attest:

RUTH C. MASON
Attesting Officer

DONALD W. BANNER
Commissioner of Patents and Trademarks